United States Patent [19]

Wagner

[11] Patent Number: 4,733,166

[45] Date of Patent: Mar. 22, 1988

[54] APPARATUS FOR MEASURING THE MOISTURE CONTENT OF MOVING MATERIALS

[76] Inventor: Delmer W. Wagner, 326 Pine Grove Rd., Rogue River, Oreg. 97537

[21] Appl. No.: 840,154

[22] Filed: Mar. 17, 1986

[51] Int. Cl.[4] .................... G01R 27/26; G01N 27/22
[52] U.S. Cl. ................................ 324/61 R; 324/61 P
[58] Field of Search .................... 324/61 R, 61 P, 65, 324/54; 73/159; 340/675

[56] References Cited

U.S. PATENT DOCUMENTS

| | | | |
|---|---|---|---|
| 3,339,137 | 8/1967 | Perry | 324/61 R |
| 3,448,381 | 6/1969 | Perry | 324/61 P |
| 3,811,087 | 5/1974 | Schmelzer | 324/61 P X |
| 4,027,238 | 5/1977 | Loch | 324/65 R |
| 4,377,783 | 3/1983 | Wagner | 324/61 R |
| 4,493,039 | 1/1985 | Gregory | 324/61 R X |
| 4,563,635 | 1/1986 | Wagner et al. | 324/61 R |
| 4,683,418 | 7/1987 | Wagner et al. | 324/61 R X |

Primary Examiner—Gerard R. Strecker
Attorney, Agent, or Firm—Dellett, Smith-Hill and Bedell

[57] ABSTRACT

Moisture in wood veneer strips received from a drying oven is measured by passing the veneer strips on a conveyor between arrays of conducting elements including a pair of transmitting bars on one side of the veneer and a pair of receiving plates juxtaposed therewith on the other. The transmitting bars are energized with signals out of phase with respect to each other on either side of ground, and the receiving plates are likewise disposed to receive the phased signals. When wet veneer passes between the plates arrays, part of the transmitted signal is shunted through the veneer, reducing the signal received by the receiving plates.

11 Claims, 6 Drawing Figures

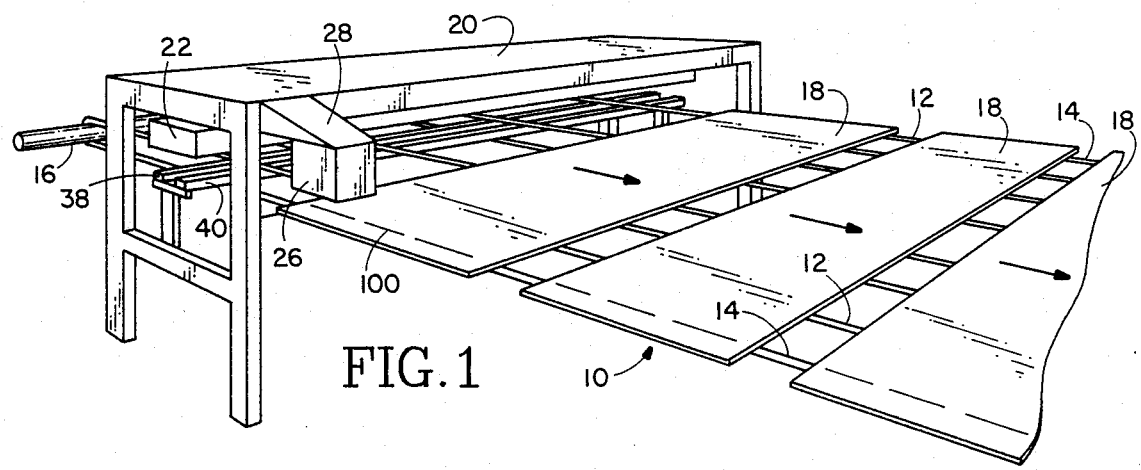
FIG. 1
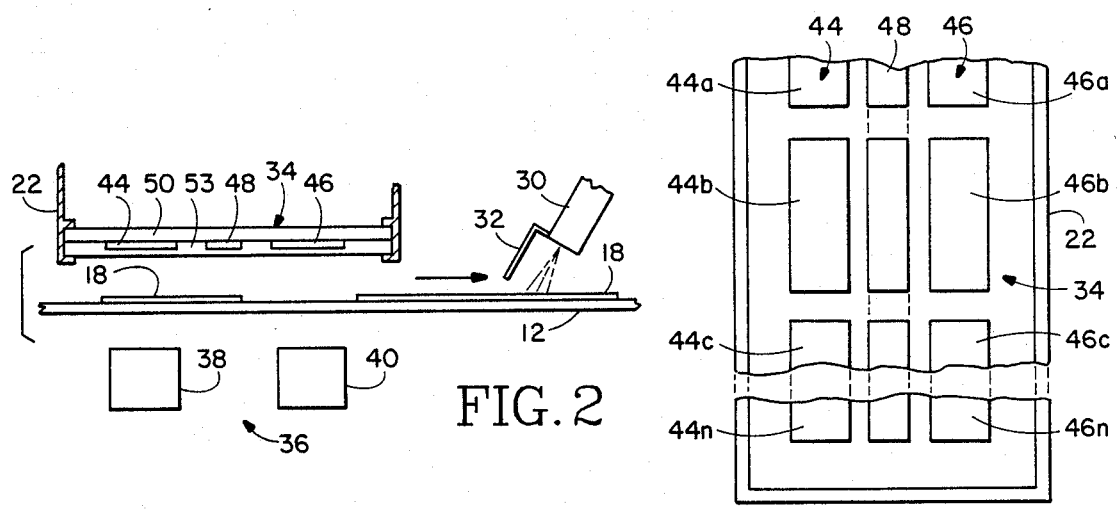
FIG. 2
FIG. 3
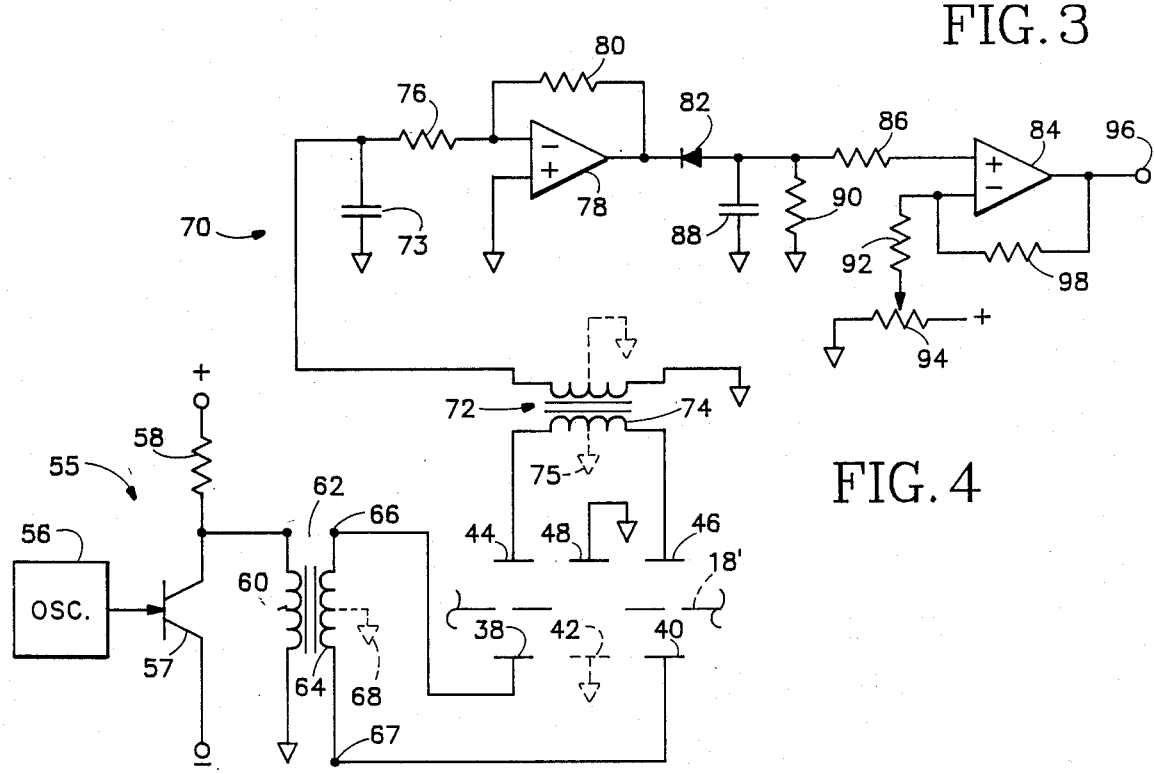
FIG. 4

APPARATUS FOR MEASURING THE MOISTURE CONTENT OF MOVING MATERIALS

BACKGROUND OF THE INVENTION

The present invention relates to moisture detectors, and particularly to an improved method and apparatus for non-contact measuring of moisture in moving material.

Moisture measuring devices typically employ a means for contacting the material being tested to establish a conductive connection, so that moisture in the material can be detected by electrical conduction. Unfortunately, the contacting means, typically brushes, are subject to damage, breakage and electrical shorting whereby the moisture indications tend to become erratic and inaccurate. Further, even if the brushes are in good condition, the degree of electrical contact provided with the material under test is often nonuniform.

Moisture detectors have been developed which do not require contact with the material being tested, but instead employ capacitive coupling or the like. Many such detectors, however, are quite sensitive to the position of the moving material relative to the sensor conductor, as well as to the thickness of the material, and therefore indications derived on a production-line basis can be somewhat undependable. Furthermore, the conveying means upon which the material is transported can short-circuit the measuring system such that a dependable reading cannot be obtained.

U.S. Pat. No. 4,377,783 discloses a measuring system for detecting moisture in wood veneer wherein transmitting and receiving plates are offset along the path traversed by the material being measured, and a conductive path to ground through the veneer and the conveyor moving the veneer is employed as part of the detection circuit. While efficacious, there is some dependency upon accurate contact with the material being measured.

U.S. Pat. No. 4,563,635 discloses a system for measuring moisture in wood veneer strips wherein the strips pass between arrays of plates including a transmitting plate on one side of the veneer and a receiving plate juxtaposed on the other. Phase plates on either side of and coplanar with the transmitting plate are energized by a signal having the reverse phase to that applied to the transmitting plate. When wet veneer passes between the plate arrays, part of the transmitted signal is shunted, reducing the signal received by the receiving plate. While this approach reduces sensitivity to vertical position of the veneer strips, eliminates problems associated with accidental grounding of the veneer, and obviates the need for mechanical contact with the veneer, in practice, some unwanted signal coupling occurs as a veneer sheet initially enters and then leaves the measuring region between the plate arrays, resulting in a false moisture detection signal.

U.S. patent application Ser. No. 638,020, now U.S. Pat. No. 4,683,418, assigned to the same assignee as the instant invention, provides one solution to the above-noted problem wherein transmitter bars connected to earth ground face the veneer opposite sensor plates phased with respect to signal ground; however, the bars ordinarily should be spaced relatively far apart making it somewhat difficult to detect moisture in small pieces of veneer.

It would therefore be desirable to provide a moisture measuring method and apparatus which are relatively insensitive to positioning of varying sized veneer along the path between the transmitting and receiving conductor arrays.

It is an object of the present invention to provide an improved method and apparatus for detecting moisture in wood veneer or the like.

It is a further object of the present invention to provide an improved method and apparatus for detecting moisture in an object in a manner less sensitive to physical position of the object.

SUMMARY OF THE INVENTION

According to the present invention, in accordance with a preferred embodiment thereof, the material, such as wood veneer or other material in which moisture is to be detected, is transported along a path into a region between a transmitting conductor means and a receiving conductor means that are relatively juxtaposed to one another. The conductor means are laterally spaced apart along the path with respect to each other and in out-of-phase relation to each other with respect to signal ground.

DRAWINGS

While the invention is set forth with particularity in the appended claims, other objects, features, the organization and method of operation of the invention will become more apparent, and the invention will best be understood, by referring to the following detailed description in conjunction with the accompanying drawing in which:

FIG. 1 is a perspective view of moisture detecting apparatus according to the present invention;

FIG. 2 is a longitudinal cross-sectional view of such apparatus;

FIG. 3 is a top view of an upper cabinet of FIG. 2;

FIG. 4 is a schematic diagram of circuitry according to the moisture detecting apparatus of the present invention;

DESCRIPTION OF THE PREFERRED EMBODIMENT

Figure 5:
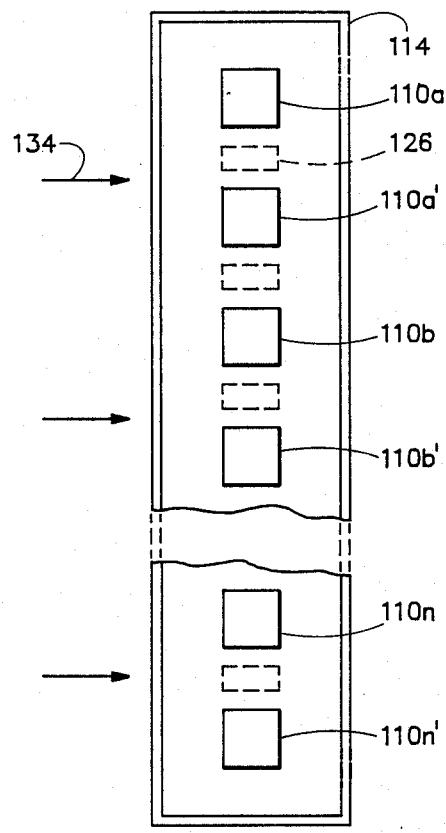
FIG. 5 is a top view of a lower cabinet according to an alternative embodiment of the invention.

Referring now to the various views of the drawing for a more detailed description of the construction, function, operation and other features of the instant invention by characters of reference, and particularly FIGS. 1–4 illustrating moisture detecting apparatus, a conveyor 10 comprises forwardly moving upper parallel conveyor elements or runs 12 and lower return runs 14, suitably comprising chains or belts which pass around an end shaft 16. The end shaft 16 may incorporate a plurality of sprockets or the like for engaging the conveyor elements 12,14. The conveyor 10 receives a plurality of plywood veneer strips or pieces 18 from a veneer dryer, not shown, which strips or pieces 18 are deposited upon the conveyor proximate the end shaft 16 and passed in the direction indicated by the arrows between the legs of a rectangular support table 20.

The table 20 carries therebeneath an upper elongated metal cabinet 22 disposed above the conveyor runs 12, 14 in crossways relation thereto, and lower transmitting bars 38, 40 positioned between the conveyor runs 12, 14 and in parallel relation beneath the length of upper cabinet 22. The table 20 also carries adjacent its rearward side a hood 26 supported from the table by a bracket 28, the hood 26 enclosing a sprayer 30 for marking veneer strips in which a predetermined amount of moisture is detected. The sprayer 30 is suitably provided with a paint shield 32 on the rearward side thereof, and is otherwise similar to the spray head disclosed in aforementioned U.S. Pat. No. 4,377,783.

Referring to FIGS. 2 and 3, supported at the bottom of the upper cabinet 22 extending for the width of the conveyor is receiving plate array 34 comprising a plurality of conducting receiving metal plates longitudinally disposed with respect to the cabinet and in facing relation to the veneer strips 18 conveyed thereunder. Bars 38, 40 comprise a lower conductive array 36 wherein bar 38 is in substantial juxtaposition with a number of plates 44 and bar 40 is in substantial juxtaposition with a number of plates 46. Each of the bars 38, 40 is suitably 2¼ inches wide with a length comparable to that of table 20. Receiving plates 44 and 46 are suitably two inches wide by ten inches long, being laterally spaced apart, with each pair 44n-1, 46n-1 being longitudinally spaced from the next pair 44n, 46n. Ground plates 48 are disposed intermediate and coplanar with the receiving plates 44, 46, such that a piece of veneer 18 traversing the support table passes between first transmitting bar 38 and first receiving plates 44a, 44b, . . . 44n, then under ground plates 48, and then between bar 40 and second receiving plates 46a, 46b . . . 46n. The ground plates 48 in the specific example are about two inches wide and spaced about 2.5 centimeters from each of the receiving plates 44, 46. Ground plates 48 may have the same longitudinal dimension as the receiving plates or may constitute one continuous plate (as indicated in dashed lines) which is comparable in length to the length of the cabinet 22. The ground plate 48 may in some cases be omitted, or, if desired, a juxtaposed ground bar may be disposed laterally between and parallel to bars 38, 40.

The plate array 34 suitably comprises printed or etched conductors on a circuit board section 50 composed of epoxy glass and forming the bottom of the cabinet 22. The printed circuit board 50 is covered with a layer 53 of an insulative substance such as polyester resin which provides a protective shield approximately one-half centimeter thick over the conductors. Thus, when mounted in the cabinet, the conducting plates are well insulated and protected from damage.

The top runs 12 of the conveyor are positioned so that the strips of veneer 18 will be disposed approximately halfway between the transmitting and receiving conductors. The spacing between the conductive arrays 34, 36 is relatively wide, in a typical instance approximately eleven centimeters, providing a spacing which is suitable for measuring moisture in wood having a thickness from a fraction of a centimeter up to about five centimeters, the conveyor and/or the cabinets being adjusted so that the wood strips are approximately midway between the conductive arrays 34, 36.

Referring to FIG. 4, a circuit is illustrated for the moisture detector according to the present invention. While the ensuing discussion describes a circuit with reference to one pair of transmitting conductors and one pair of receiving conductors, it is understood that each pair of receiving plates may be connected to duplicate receiving circuitry for operation in a like or similar manner as described herein.

A signal transmitting means 55 includes an alternating current signal source or oscillator 56, suitably comprising a type 12060 integrated circuit manufactured by Motorola, Inc. The oscillator 56 provides its output to a gate terminal of a VMOS field effect switching transistor 57, for example comprising a type VN1OKM having a source terminal connected to a negative supply and a drain terminal connected to a positive supply through a resistor 58.

The oscillator 56 suitably operates at a frequency between five hundred hertz and two hundred kilohertz with the circuit components illustrated; however it is understood that the presently described embodiment of the invention may operate effectively at other frequencies. The oscillator 56, via the transistor 57, provides an input to primary winding 60 of a one-to-one ferrite core transformer 62 having a secondary winding 64 with output terminals 66, 67. The terminal 66 provides a transmitting signal to a transmitting bar represented at 38, while the signal at the other terminal 67, which is 180 degrees out of phase with the signal at terminal 66, is connected to the other transmitting bar represented at 40. Thus, it will be seen that the transmitting bars 38, 40 are coupled in balanced out-of-phase relation or phased 180 degrees apart with respect to each other on either side of ground, which is represented by center tap 68 as shown in dashed lines and which may comprise an actual ground connection.

A detector means 70, coupled to the receiving plates 44, 46 through a one-to-one ferrite core transformer 72, includes a tuned circuit comprising a capacitor 73 connected in parallel with the secondary winding of the transformer 72 and tuned substantially to the frequency of the signal generating means 56. The receiving plates 44, 46, as connected across primary winding 74 of the transformer 72, are on opposite sides of ground as indicated by center tap 75 of primary winding 74, which center tap may comprise a physical ground connection. The signal across the tuned circuit is coupled through an input resistor 76 to a first operational amplifier 78 provided with a feedback resistor 80 and having a second input terminal which is grounded. The AC output of the amplifier 78 is detected with a diode 82 the anode of which is coupled to an input of a comparator amplifier 84 through a resistor 86 and shunted to ground through a capacitor 88 in parallel with a resistor 90. The amplifier 84 is provided with a second input terminal coupled via a resistor 92 to a movable tap of a potentiometer 94 connected between a positive voltage and ground. An output terminal 96 of the detector circuit 70 is coupled for operating the sprayer 30 when a predetermined degree of moisture is detected in a particular veneer strip passing between the upper and lower conductive arrays.

The signal received at the plates 44, 46 is amplified by the amplifier 78 and detected by diode 82 to produce a negative voltage across the capacitor 88. A second input of comparator amplifier 84 is set by means of the potentiometer 94 to establish a threshold such that if the negative charge on the capacitor drops below a predetermined level, the output terminal 96 will, via intermediate amplifiers, not shown, operate the sprayer 30. That is, moisture is ordinarily indicated when the negative voltage on capacitor 88 decreases. A feedback resistor 98 produces a hysteresis effect so that once the sprayer starts to operate, it will continue to do so until the negative voltage across the capacitor 88 increases to a negative value greater than the value at which spraying started, whereby erratic or intermittent operation of the sprayer is prevented.

Considering the overall operation of the moisture detecting apparatus illustrated in FIGS. 1-4, the alternating current signal on the transmitting bars 38, 40 is normally coupled to the receiving plates 44, 46 in the absence of wet veneer or other conducting material in the general area between the arrays, such area being indicated by dashed line 18' in FIG. 4.

In the presence of wet veneer between the arrays of plates, moisture that extends substantially across the transmitting conductors 38, 40 has a shunting effect on the transmitted signal whereby a decreased signal is received at the receiving plates 44, 46, causing the negative voltage on capacitor 88 to decrease or become more positive so that the comparator amplifier 84 produces a signal output at the terminal 96 for operating the sprayer and marking the wood. Of course, the potentiometer 94 can be adjusted to select the correct point at which the sprayer operates.

Wet veneer at 18' provides a shielding effect relative to the receiving plates 44, 46, or a shunting effect, such that the signal field from the transmitting bars 38, 40 tends to pass between bars 38 and 40 through the wet veneer, or from the bars 38, 40 through the wet veneer to a ground bar 42, whereby the signal at the receiving plates 44, 46 is reduced in the presence of the wet material.

The present measurement method and apparatus has the advantage of enhanced immunity from inaccurate readings due to variations in wood thickness and wood position between the upper and lower arrays of plates, since the transmitted signal tends to place the wood at ground level as the transmitted signal is shunted. That is, the voltage level induced in the wood is halfway between the voltage of bar 38 and the voltage of bar 40 when the wet wood shunts the signal between bars 38 and 40. So far as the receiver plates are concerned, the signal substantially disappears when wet wood is present. Moreover, the system is balanced, and insertion of the wood partway between the transmitting and receiving arrays does not cause an erroneous reading. Thus, an uncovered out-of-phase transmitting bar or plate does not induce an opposite phase signal at the receiving array, as in previous apparatus. Rather, a smooth change in received signal output occurs as wet wood is gradually inserted between the arrays. This is in part believed due to the fact that the receiving plate array is balanced and suitably referenced (to ground) in the same manner as the substantially identical transmitting array with which it is juxtaposed. Furthermore, it is found that one or both grounds may be absent in which case the plate array or arrays will "float", still retaining the above advantages of immunity to wood position and thickness, balance, and immunity to an erroneous output reading when the leading edge of the wood starts entering the region between the arrays.

A particular veneer strip 18 passing through the conductive plate arrays will be spray painted, as indicated at 100 in FIG. 1, to mark the veneer strip so that it may be segregated from others.

Figure 6:
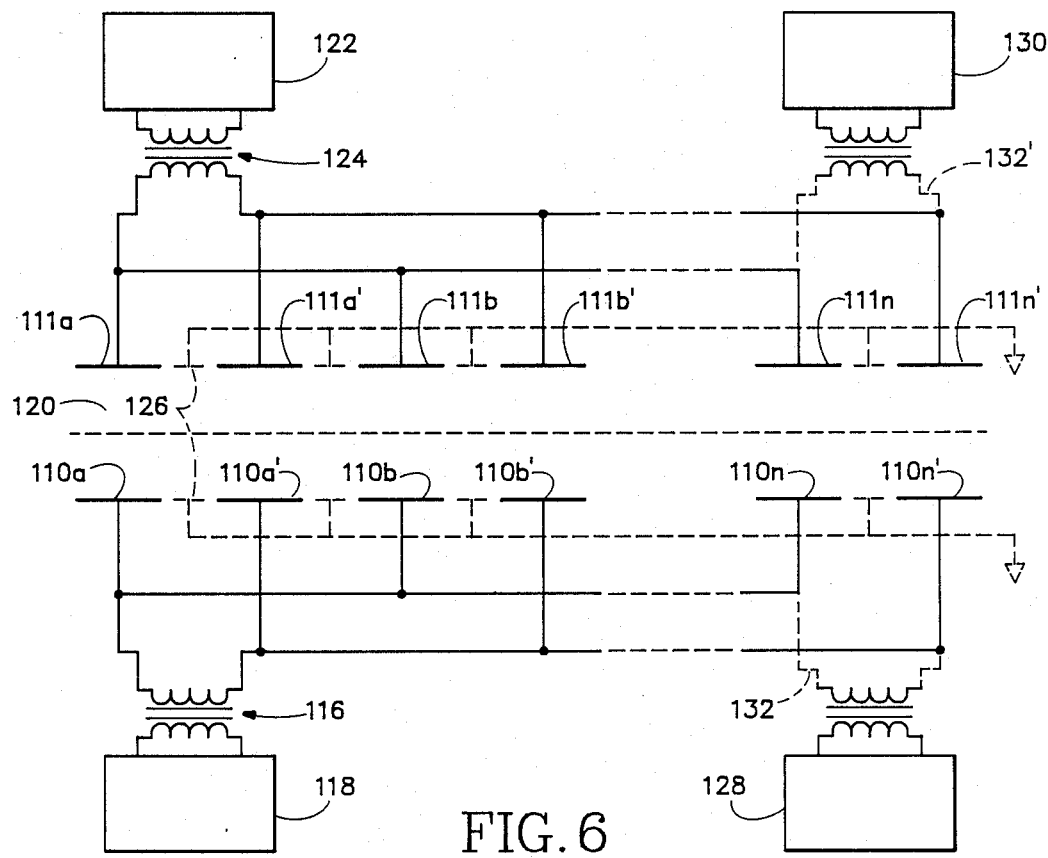
FIG. 6 is a partial schematic diagram of circuitry according to the present invention.

In accordance with an alternative embodiment of the present invention, FIGS. 5 and 6 show moisture measuring apparatus comprising a first pair of transmitting plates 110a, 110a' arranged longitudinally along a lower cabinet 114, and energized in out-of-phase relation through a transformer 116 by a signal generation means 118. Juxtaposed with the transmitting plates 110 across a space 120, through which wood veneer is passed, is a first pair of receiving plates 111a, 111a', similarly arranged longitudinally along an upper cabinet and coupled to a detector means 122 through a transformer 124. Optional ground plates, indicated by dashed lines 126, may be disposed between the respective pairs of transmitting and receiving plates 110, 111. In a specific example, the plates 110, 111 are suitably ten centimeters square, and spaced apart five to seven centimeters in the absence of ground plates 126. The ground plates, if used, are suitably five by ten centimeters, and are spaced apart from the adjacent transmitting or receiving plates by three to five centimeters.

Additional pairs of transmitting plates 110b, 110b' ... 110n, 110n' and receiving plates 111b, 111b' ... 111n, 111n' are disposed longitudinally along the cabinets in line and coplanar with the first plates 110, 111. The additional plates are suitably connected in parallel relation with the first plates to the same transformers 118, 124 to form one detector section. Alternatively, different pairs of juxtaposed transmitting and receiving plates may be connected to separate signal generating means 128 and separate detector means 130, as indicated by dashed lines 132, 132', to form another detector section. In the presently described embodiment of the invention, detector sections having a length of approximately sixty centimeters have been found to be most efficacious. It will be observed that the wood veneer passes the linear plate array of this embodiment in the direction indicated by the arrows 134 of FIG. 5. However, it should be noted that in either embodiment the material being tested may be conveyed in a direction perpendicular or parallel or for that matter with any orientation to the conductive arrays. The transmitter and receiver connections and the general construction and operation of the moisture detector of the second embodiment are substantially similar to the previous embodiment.

While the principles of the invention have now been made clear from the foregoing illustrative embodiments, there will be immediately obvious to those skilled in the art many modifications of structure, arrangement, proportions, the elements, material and components used in the practice of the invention, and otherwise, which are particularly adapted for specific environments and operating requirements without departing from those principles. The appended claims are, therefore, intended to cover and embrace any such modifications, within the limits only of the true spirit and scope of the invention.

I claim:

1. Apparatus for measuring moisture content of moving material, said apparatus comprising:

means for generating an alternating electrical signal;

first conductor means disposed in facing relation to a first side of said moving material for transmitting the alternating electrical signal;

second conductor means disposed in facing relation to the first side of said moving material in laterally spaced relation to said first conductor means for transmitting the alternating electrical signal;

means for coupling said signal generating means to said first and said second conductor means, said first conductor means being in balanced out-of-phase relation with respect to said second conductor means;

third and fourth conductor means disposed in facing relation to a side of said material opposite said first side and opposite, respectively, said first and said second conductor means, for receiving said alternating electrical signal transmitted from said first and second conductor means;

output circuit means for detecting a predetermined level of said alternating electrical signal received in said third and fourth conductor means; and means for coupling said output circuit means to said third and fourth conductor means, said third conductor means being in balanced out-of-phase relation with repect to said fourth conductor means, whereby moisture in said moving material disposed between the oppositely facing conductor means can be detected according to signal shunting in said material, and whereby a smooth transition of output signal occurs as moist moving material enters and traverses between the oppositely disposed conductor means.

2. The apparatus according to claim 1 further comprising:

grounded fifth conductor means in facing relation to the first side of said moving material and spaced apart laterally from and intermediate said first and second conductor means; and grounded sixth conductor means in facing relation to the opposite side of said moving material and spaced apart laterally from and intermediate said third and fourth conductor means.

3. Apparatus for measuring moisture content of moving material between first and second sides of said material, said apparatus comprising:

means for generating an alternating electrical signal;

first conductor means disposed in facing relation of the first side of said material for transmitting the alternating electrical signal;

second conductor means disposed in facing relation to the first side of said material in laterally spaced relation to said first conductor means for transmitting the alternating electrical signal;

means for coupling said signal generating means to said first and second conductor means, said first conductor means being in out-of-phase relation with respect to said second conductor means;

at least third conductor means disposed in facing relation to the second side of said material and opposite said first conductor means for receiving said alternating electrical signal transmitted from said first and said second conductor means; and output circuit means coupled to said third conductor means for detecting the moisture content of said moving material disposed between said first and third conductor means according to the amount of shunting in said moving material of said transmitted alternating electrical signal, said receiving means being electrically referenced to a same level as said second conductor means.

4. Apparatus for measuring moisture content of moving material, said apparatus comprising:

means for generating an alternating electrical signal;

a first conductive array including a first transmitting bar disposed in facing relation to a first side of said moving material, a second transmitting bar disposed in facing relation to the first side of said moving material in spaced relation and coplanar with said first transmitting bar, and a first receiving plate array including first and second coplanar receiving plates disposed in facing relation to a side of said moving material opposite said first side and opposite, respectively, said first and said second transmitting bars;

first means for coupling said generating means to said first and said second transmitting bars, said first transmitting bar being in balanced out-of-phase relation with said transmitting bar, said altnerating electrical signal being transmitted to said first and second receiving plates from said first and second transmitting bars;

output circuit means responsive to said alternating electrical signal coupled to said first and second receiving plates for detecting a predetermined level of said alternating electrical signal received in said first and second receiving plates; and second means for coupling said output circuit means to said first and second receiving plates, said first receiving plate being in balanced out-of-phase relation with said second receiving plate, whereby moisture in said material disposed between the oppositely facing plates can be detected according to signal shunting in said material.

5. The apparatus according to claim 4 wherein said moving material traverses said apparatus simultaneously between both said transmitting bars and both said receiving plates.

6. The apparatus according to claim 4 wherein said moving material traverses said apparatus successively between said first bars and plates, and then said second bars and plates.

7. The apparatus according to claim 4 wherein said first conductor array further comprises:

a first ground conductor intermediate said first and second transmitter bars; and a second ground conductor intermediate said first and second receiving plates.

8. The apparatus according to claim 4 further comprising a second conductive array substantially like said first conductive array, said second conductive array being in lateral spaced relation with said first conductive array, bars and plates of said second conductive array being connected in parallel relation with the corresponding bars and plates of said first conductive array, respectively, to said first and second coupling means.

9. The apparatus according to claim 4 further comprising a second receiving plate array substantially similar to said first receiving plate array, said second receiving plate array being in lateral spaced relation with said first receiving plate array, the plates of said second receiving plate array being coupled to additional output circuit means.

10. The apparatus according to claim 4 further comprising:

a second receiving plate array similar to said first mentioned receiving plate array, said second receiving plate array being in lateral spaced relation with said first receiving plate array;

additional output circuit means for detecting a predetermined level of said alternating electrical signal received in the receiving plates of said second receiving plate array; and third means for coupling said additional output circuit means to the receiving plates of said second receiving plate array, said first receiving plate of said second receiving plate array being in balanced out-of-phase relation with said second receiving plate of said second receiving plate array, whereby moisture in said material disposed between adjacent plates of said second receiving plate array can be detected according to signal shunting in said material.

11. The apparatus according to claim 10 wherein said conductive array further comprises:

a ground conductor intermediate said first and second transmitter bars; and
a ground plate intermediate said first and second receiving plates.

* * * * *

UNITED STATES PATENT AND TRADEMARK OFFICE
CERTIFICATE OF CORRECTION

PATENT NO. : 4,733,166
DATED : March 22, 1988
INVENTOR(S) : DELMER W. WAGNER

It is certified that error appears in the above-identified patent and that said Letters Patent is hereby corrected as shown below:

On the title page:
In the Abstract, line 10, "plates" should be --plate--.

Column 7, line 32, "of" should be --to--.

Column 8, line 6, between "said" and "transmitting" insert --second--.

Column 8, line 6, "altnerating" should be --alternating--.

Signed and Sealed this

Twenty-eighth Day of July, 1992

*Attest:*

DOUGLAS B. COMER

*Attesting Officer*     *Acting Commissioner of Patents and Trademarks*